Feb. 21, 1967 E. McDADE Plant Pat. 2,716
ORCHID PLANT
Filed Jan. 21, 1965
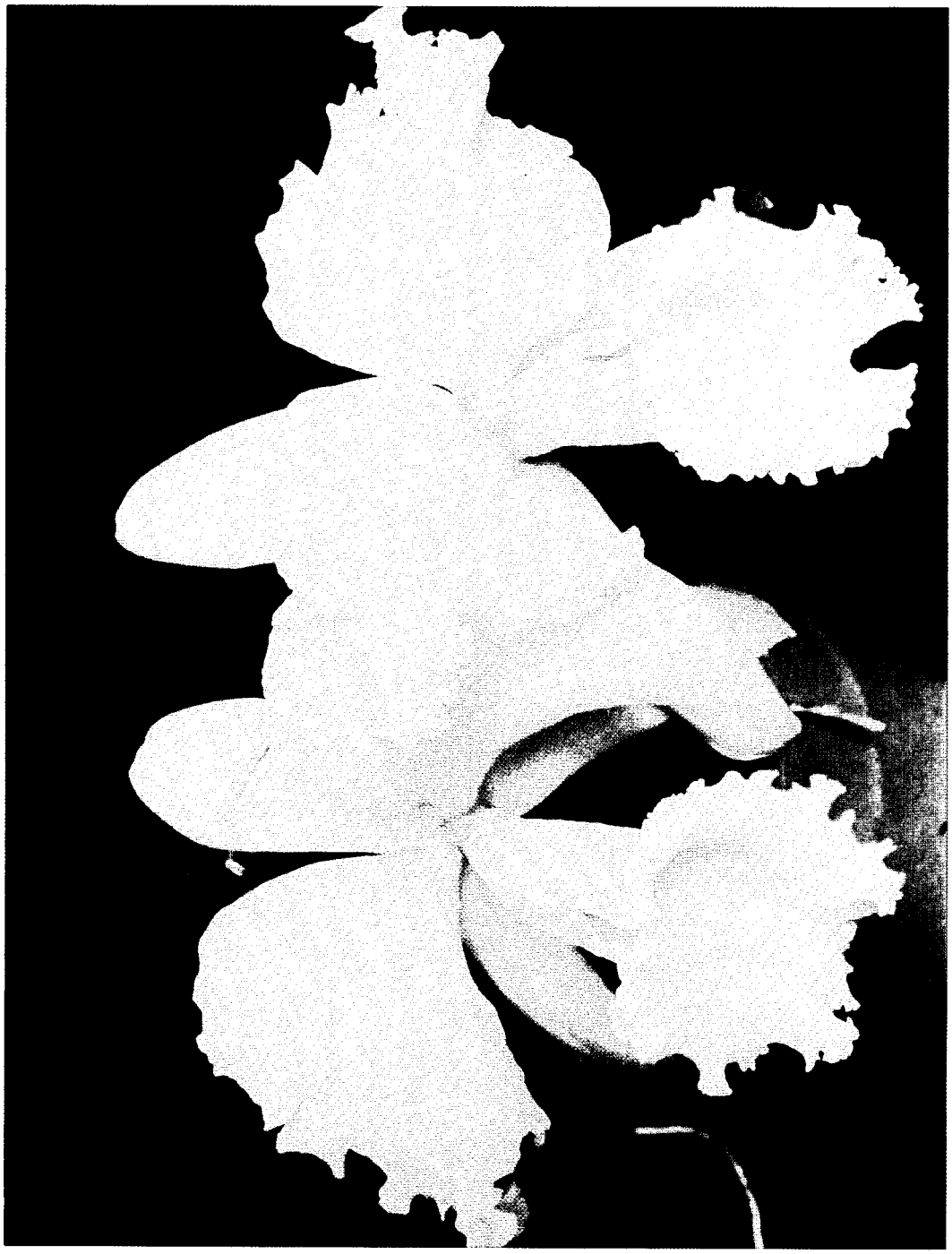
Everest McDade
INVENTOR.
BY Clarence A. O'Brien and Harvey B. Jacobson
Attorneys United States Patent Office Plant Pat. 2,716
Patented Feb. 21, 1967

2,716
ORCHID PLANT

Everest McDade, 344 Royal Pines Drive,
Skyland, N.C. 28776

Filed Jan. 21, 1965, Ser. No. 427,194
1 Claim. (Cl. Plt.—68)

The subject invention relates to a new and distinct variety of Cattleya orchid. The plant was obtained by self-pollination of an outstanding orchid plant, Cattleya Bow Bells, variety Honolulu (unpatented). Cattleya Bow Bells, variety Honolulu was among the plants of a cross between *Cattleya edithiae,* variety White Empress, and a variety of Cattleya Suzanne Hye, which cross was made by Black and Flory, Ltd., Slough, Bucks, England, and registered by them in the April 1945 Orchid Review.

All the seedlings grown from the self-pollinated plant were designated as Cattleya Bow Bells, Honolulu strain. Several plants of the Honolulu strain were selected because of their responsiveness to reproduction by apical meristem tissues culture.

One particular plant was selected from the several clones produced by tissue culture because it had been reproduced in sufficient numbers (400) to be of commercial value, the clone flowered first and the flowers were desirable.

The drawing shows the plant and flower of a fully developed orchid of the new variety claimed.

My new variety has the following characteristics:

*The plant*

The flowering sized plant of seven years' growth consists of a colony of five or more stems, each stem 12 inches in height and two ounces in weight.

The roots are moderately branching with the advantage that terminal root tips, if damaged during transplanting, are soon replaced by lateral root tips emerging from damaged roots.

The variety is propagated by division of mature plants, yielding an increase of 40% weight per year. Propagation of immature plants is much more rapid, especially when the tissure culture method is employed.

Thirty sequential stems have grown from one another without change in the character of the flowers borne on each stem.

Adult stem: Seven segments as viewed from bottom, and one leaf at top of segment #7. Stem buds are visible at tops of segments #3, #4 and #5. Bud of segment

#4 active, bud #3 dormant, and bud #5 usually dormant.

Adult stem measurements: Natural height from bottom of rhizome, 13″. Top stem segment #7, 4.3″ side measurement. Leaf upper side width, 2.8″. Leaf underside length, 9.1″.

Roots: Four each on segments #2, #3, #4, and an occasional root on segment #5.

*Flowers*

There are two or three flowers per bloom spike with diameters of six inches, each flower weighing about 18 grams. The flowers are distinctly larger and heavier than the currently marketed varieties.

The natural flowering season occurs when stem growths mature during summer and flower in September. Growths maturing at other seasons flower when mature. The bloom season of these sensitive short-day plants may be deferred by illumination from incandescent lights.

Color:

Flower Measurements, front view projected lengths in inches.

*Natural spread.*—7.0″.

*Petals.*—2.9″ wide—3.6″ radius from center.

*Lateral sepals.*—1.0″ wide—4.1″ radius from center.

*Dorsal sepals.*—Scarcely visible from front view.

Color of flower: Ostwald Color System, Color Harmony Manual, Container Corp. of America, Chicago, Illinois).

*Sepals.*—White.

*Petals.*—White.

*Lip.*—PA3 (yellow-orange) in center of lip.

This variety is distinctively different in the unusual color pattern comprising two cresecent shaped white areas in yellow portion of lip and by the faintly tree-lobed petal shape.

Texture: Very thick and rigid.

Having thus disclosed my invention, I claim:

A new and distinct variety of orchid plant, substantially as shown and described, characterized particularly by its two crescent shaped white areas in yellow portion of lip; its faintly three-lobed petal shape; its rapid multiplication and exceptionally large and heavy flowers and its branching roots and light controlling flowering season.

No references cited.

ABRAHAM G. STONE, *Primay Examiner.*

R. E. BAGWILL, *Assistant Examiner.*